United States Patent
Tsang et al.

(10) Patent No.: US 6,558,899 B1
(45) Date of Patent: *May 6, 2003

(54) METHOD FOR IDENTIFYING NEW ANTI-PICORNAVIRAL COMPOUNDS

(76) Inventors: Simon K. Tsang, 12 Arlington St., Cambridge, MA (US) 02140; Diane M. Joseph-McCarthy, 35 Pond St., Belmont, MA (US) 02178; James M. Hogle, 32 Leonard Ave., Newton, MA (US) 02165

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/210,118

(22) Filed: Dec. 11, 1998

Related U.S. Application Data

(60) Provisional application No. 60/069,302, filed on Dec. 11, 1997.

(51) Int. Cl.⁷ ................................................. C12Q 1/70
(52) U.S. Cl. ............................ 435/5; 435/7.8; 436/518
(58) Field of Search ........................ 435/5, 7.8; 436/518

(56) References Cited

U.S. PATENT DOCUMENTS 5,891,742 A * 4/1999 Dollinger et al. ........... 436/538

FOREIGN PATENT DOCUMENTS

WO     WO 96/22530     * 7/1996

OTHER PUBLICATIONS

Andries et al., Two groups of rhinoviruses revealed by a panel of antiviral compounds present sequence divergence and differential pathogenicity. J. Virol. 64(3):1117–1123, 1990.*

Grant, R.A., et al., *Curr. Biol.*, 4:784 (1994).

Joseph–McCarthy, D., et al., *Proteins*, 29:32–58 (1997).

Rueckert, R.R. and Pallansch, M., *Methods in Enzymol.*, 78:315–325 (1981).

Schumacher,T.N., et al., *Science*, 271:1854 (1996).

Shuker, S.B., et al., *Science*, 274:1531 (1996).

Smith, T.J., et al., *Science*, 233:1286 (1986).

* cited by examiner

*Primary Examiner*—Donna C. Wortman
(74) *Attorney, Agent, or Firm*—Hamilton, Brook, Smith & Reynolds, P.C.

(57) ABSTRACT

The present invention is broadly directed to methods of screening viral-binding compounds. In particular, the present invention provides cell-free assays to rapidly screen libraries of compounds for viral-capsid binding activity. Such compounds are useful for anti-viral treatments.

22 Claims, 7 Drawing Sheets

FIG. 2
Mass spectrum of Janssen drugs released from virus

METHOD FOR IDENTIFYING NEW ANTI-PICORNAVIRAL COMPOUNDS

This application claims the benefit of U.S. Provisional Application No. 60/069302, filed Dec. 11, 1997.

This work was partially supported by the U.S. government under NIH grants U01 AI-32480 and R37 AI-20566. The U.S. government retains certain rights in this invention.

BACKGROUND OF THE INVENTION

1. Field of the Invention

The present invention is broadly directed to methods of screening viral-binding compounds. In particular, the present invention provides cell-free assays to rapidly screen libraries of compounds for viral-capsid binding activity. Such compounds are useful for anti-viral treatments.

2. Description of Related Art

Picornaviruses represent a very large virus family of small ribonucleic acid-containing viruses responsible for many serious human and animal diseases (Rueckert, R. R. Virology, 2nd ed. (Field, B. N. et al., eds.) Raven Press, Ltd., New York, p. 508–548 (1982)). Picornaviruses include four major genera: enteroviruses, rhinoviruses, cardioviruses and aphthoviruses. The enterovirus genus includes polioviruses and Coxsackieviruses, echoviruses, and four numbered human enterovirus species.

Poliovirus is the etiologic agent of the disease poliomyelitis in humans. The human rhinoviruses consist of at least 100 serotypes and are the primary causative agents of the common cold. The Coxsackieviruses (24 group A serotypes, 6 group B serotypes), echoviruses (34 serotypes) and human enteroviruses (four serotypes), are associated with a wide range of human diseases including summer flus, diarrhea, meningitis, hepatitis, pneumonitis, myocarditis, pericarditis, and diabetes (Melnick, J. L. Virology, 2nd ed. (Fields, B. N. et al., eds.) Raven Press Ltd., New York p549–605). These infections occur sporadically in the general population, but are becoming more common among children in day care and their parents and siblings. In general, the available drugs have either failed to demonstrate sufficient prophylactic effect or are converted in the body into inactive metabolites.

The current drugs have all been derived from the same parent compound that was found through large-scale random screening of known chemicals for activity against the virus. Such screening procedure is a very expensive and time-consuming process. There is a need in the art to develop quick and efficient assays to screen for anti-viral compounds. In particular, there is a need in the art to establish cell-free assays for screening viral-binding compounds, e.g., picornaviral-binding compounds and libraries of such compounds.

SUMMARY OF INVENTION

It is an object of the invention to provide a method for screening viral-binding compounds.

This and other objects of the invention are provided by one or more of the embodiments provided below.

In one embodiment of the invention there is provided a method for screening viral-binding compounds which comprises the steps of incubating in vitro one or more compounds with a viral site, wherein binding of a compound to the viral site inhibits viral infection, separating a viral site-bound compound from an unbound compound, and detecting the viral site-bound compound. In a preferred embodiment, the viral site is contained within a viral capsid.

The present invention provides in vitro assays for rapid screening of anti-viral compounds, especially viral-binding compounds. Such compounds can be therapeutically effective in anti-viral treatments.

BRIEF DESCRIPTION OF THE DRAWINGS

FIG. 2 shows a mass spectroscopy analysis of drugs released from virus.

DETAILED DESCRIPTION OF THE INVENTION

Figure 1:
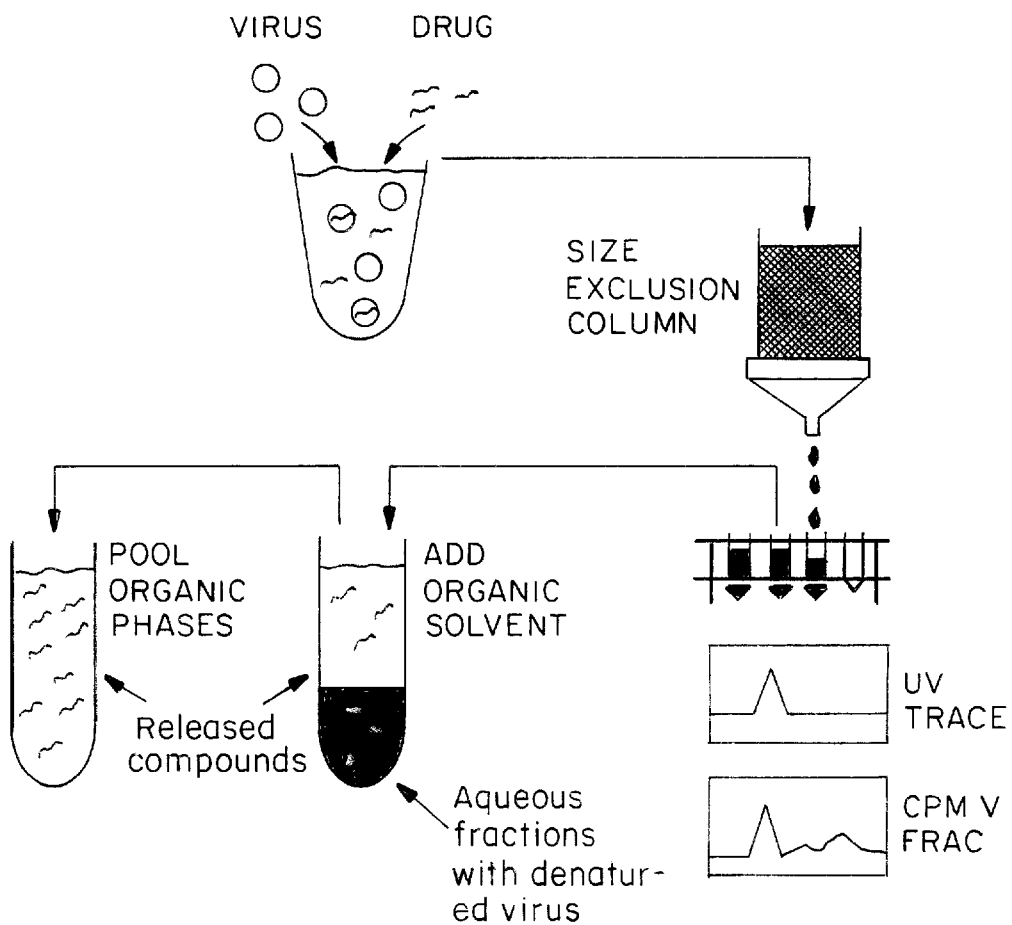
FIG. 1 shows a schematic drawing of the virus binding assay.

The present invention provides a high-throughput in vitro assay that can rapidly screen libraries of compounds for specific binding to a viral target. Libraries of hundreds or thousands of compounds can be simultaneously screened by the cell-free assays described in the present invention within a very short period of time, e.g., a few hours. The viral-binding compounds detected by the screening assays of the present invention are potential therapeutic compounds for anti-viral treatments.

This method may be generally used to screen for binding to any nonenveloped virus (including picornaviruses, caliciviruses, parvoviruses, papovaviruses (e.g., papillomaviruses), reoviruses and adenoviruses) whose intact virions may be isolated by techniques obvious to those skilled in the art (see Luria, S. E., et al. General Virology, 3rd ed., John Wiley & Sons, New York p33–34 for general methods of virus purification, and relevant chapters and references therein in Fields, B. N. et al., Fundamental Virology 3rd edition, Lippincott-Raven, New York 1996 for propagation and purification of specific virus groups), or for any enveloped virus (including HIV, hepatitis B and herpes viruses) which contain a stable nucleocapsid particle which can be isolated by those skillful in the art (Luria, S. E. et al., supra; Fields, B. N. et al., supra).

A viral site is used as a probe in the cell-free screen assays of the present invention. The viral sites used in the assay can be in their isolated form or contained within a virus or part of a virus, e.g., viral capsid. The viral site can be any viral region or binding pocket in any component of a virus that is involved in viral infection, e.g., viral activation, replication, and structure rearrangements. Any viral site for which compound binding inhibits viral infection is contemplated in the present invention. For example, the viral site may be those that constitute the viral capsid or binding sites for known anti-viral compounds.

Binding sites for anti-viral compounds are known and can be easily obtained. For instance, crystallographic studies on various strains of poliovirus and rhinovirus have shown that known anti-picornaviral compounds bind to a conserved, hydrophobic pocket at the core of VP1 which is one of four proteins constituting the viral capsid. Tight binding of a therapeutic compound in this pocket could prevent structural rearrangements in VP1 and the subsequent transition of the mature virus into an infection intermediate. Such a conserved hydrophobic pocket at the core of viral capsid proteins, e.g., VP1, can be used as target site for the screening assays of the present invention.

The initial phase of the screening assay involves the incubation of viral sites with libraries of compounds to allow for the specific interaction between the compounds and the viral sites. The amount of virus and drug used in the incubation may be adjusted in order to maximize the sensitivity or the specificity of the assay. In general, the amount of virus and therefore the number of sites will be limiting, and must be adjusted such that the total number of sites are sufficient to guarantee detection of a bound compound. The amount of compound used in the screening assay is usually in the micromolar to nanomolar range. Preferably, it is from about 1 $\mu$M to about 400 $\mu$M, more preferably from about 50 $\mu$M to about 200 $\mu$M, and most preferably from about 100 $\mu$M to 200 $\mu$M. The amount of viral binding sites used is related to the amount of compounds, the recovery rate of the complexes, and the limitation of the detection method used. The ratio of the amount of compounds to viral sites can be varied from about 500:1 to about 1:1, preferably from about 100:1 to about 10:1. The ratio of the concentration of compounds to viral sites may be adjusted as needed to detect up to a specific number of binders given the sensitivity of the detection system. Alternatively the ratio of compounds to viral sites may be increased in order to allow detection of binding in cases where all compounds in a library bind weakly. The appropriate amounts of virus and compound-to-virus ratios easily may be determined by one skilled in the art.

The incubation of viral sites and compounds may be carried out at room temperature for a few hours, e.g., one to four hours or at 4° C. for a longer period of time, e.g., overnight. Different viral sites may require different incubation temperature and incubation time. Such conditions can be easily determined by one skilled in the art.

The viral site-bound compounds can be separated from unbound compounds via any means known in the art. For example, the compound-virus complexes may be isolated by loading the incubation mixture onto a size exclusion column, e.g., a Sephacryl S-200 or S-300 column, developing the column and selecting the fraction containing virus as indicated by absorption at 280 nm. The bound compounds may then be extracted from the isolated compound-virus complexes via any means known in the art. For example, the compounds may be extracted by differential solvent extraction of the isolated complexes, for example by extraction with ethyl acetate or any appropriate solvent which is not miscible in water. Mass spectroscopy is usually used to detect and identify the compounds which have been extracted from the compound-virus complexes. Typically, electro-spray mass spectroscopy or matrix assisted laser desorption ionization time-of-flight (MALDI-TOF) mass spectroscopy are used.

The following examples are provided for exemplification purposes only and are not intended to limit the scope of the invention which has been described in broad terms above.

EXAMPLE 1

Formation of Virus-Compound Complexes

The initial phase of the assay involves the incubation of virus with libraries of compounds to allow for the specific interaction between the compounds and virus. Poliovirus (P1/Mahoney, or P1/M) is grown in HeLa cells and purified by differential centrifugation and CsCl density gradient fractionation according to standard methods (Rueckert, R. R. and Pallansch, M., Methods in Enzymol. 78:315–325 (1981)). The virus is stored frozen in phosphate buffered saline (PBS) at −80° C. until use. Stock solutions of the virus are in PBS, while mixtures of potential ligands are dissolved in DMSO. These stock solutions are diluted such that all incubations are carried out at a final DMSO concentration of 5% in PBS. Final volumes ranged from 0.5 to 1.0 mL. Once mixed, the incubations were left at room temperature for one to four hours or kept at 4° C. overnight (See FIG. 1 for schematic).

The sensitivity of the assay is largely dictated by two factors: (1) the amount of virus used, which determines the number of available virus binding sites, and (2) the current detection limit of mass spectroscopy (MS). For our electrospray mass spectrometer, this limit is 50 picomole/25 $\mu$L or 2 $\mu$M. In the case of MALDI-TOF MS, the mass spectrometer at our disposal has a limit of approximately 1 picomole. Using our MALDI-TOF MS, therefore, to select ten compounds from a library of indefinite size requires 10 picomoles of viral sites (see below for recovery rates). A typical experiment requires between 0.1 and 0.8 mg of virus in 0.5 mL incubation mixture.

Detection of virus-compound complex formation largely depends upon two factors. First, the concentration of the compound in the incubation must be above a critical threshold. Existing anti-picornaviral compounds work in the micromolar to nanomolar range. The estimated concentration of compound in the typical stock solutions of existing libraries is $6 \times 10^{-3}$M. Screens have been carried out with the total concentration of compound in the incubation ranging from 10 to 350 $\mu$M. Complex formation can be driven by increasing the number of drug molecules per viral binding sites. In so doing, a competition results between compounds in the library for the available binding sites. Those compounds which have the highest affinity for the pocket, i.e., viral binding site will easily compete out the weaker binders and the excess compound ensures that the equilibrium of binding is shifted towards complex.

EXAMPLE 2

Purification of Virus-Compound Complexes

Virus-drug mixtures are loaded onto a size exclusion column (1.4 cm diameter×8.4 cm height) having a Sephacryl S-200 or S-300 matrix (Pharmacia) to separate virus-drug complexes from unbound drug. The running buffer is 5% DMSO in PBS. One mL fractions are collected at 0.5 mL/min. Identification of fractions containing the void volume, and therefore possibly containing viruses bound with compound, is accomplished with a Pharmacia Uvicord SII UV monitor which measures the OD280 of the material as it is pumped out of the column (See FIG. 1 for schematic).

EXAMPLE 3

Extraction and Concentration of Virus-Bound Drug

Fractions containing virus bound with compounds are mixed with a double volume of ethyl acetate, vortexed for 30 seconds, then centrifuged for 10 minutes at 12,000×g. At this point the viruses will be completely denatured. Previously virus-bound drug is released, and will partition into the ethyl acetate phase. The upper organic phase is separated from the aqueous phases. The organic phase containing the compounds is dried in a centrivap (See FIG. 1 for schematic).

EXAMPLE 4

Preparation of Sample for MS

A small volume (50 μL) of an organic solvent is added to the tube containing the dried sample. Which solvent should be used depends upon the MS technique used for the analysis. For MALDI-TOF MS, the solvent is acetonitrile or THF. In the case of electro-spray MS, it is ethanol. After the addition of solvent, the tube containing the sample is vortexed. At this point, the concentration of each virus-bound compound is at least 2 μM, high enough for detection by electro-spray MS or MALDI-TOF MS. The decision between electro-spray or MALDI-TOF depends upon the material in the sample.

EXAMPLE 5

1) Optimization of Assay Conditions with Radiolabeled Compounds

The conditions of this assay were optimized using the radiolabeled compound R77975 (Janssen Pharmaceuticals). The radiolabel enabled us to track the amount of drug recovered at each step of the assay. Briefly, in a siliconized tube 240 mL of a preparation containing 2.32 mg/mL of viral binding sites, i.e., P1/M in PBS was mixed with 15.8 mL of $2.5 \times 10^{-4}$ M $^3$H-R77975 in DMSO. The incubation volume was brought up to 500 mL and the DMSO content was 5% in PBS. The ratio of drug to viral binding sites or pockets was 1:1. This mixture was left at room temperature for 2 hours, then loaded onto the size exclusion column. Fractions 6 through 11 contained the virus as determined by UV trace.

To determine the yield of $^3$H-R77975 in each fraction, 100 mL of each fraction was transferred to a 7 mL scinitillation vial containing Ecoscint A (National Diagnostics) and counted in a Beckman 5000TD scintillation counter. 33% of the input labeled compound was found to be in the void volume and was bound to the virus. Nearly 100% of this material was recovered after the ethyl acetate separation. Subsequent concentration of this sample in the centrivap yielded 77% of the extracted compound. The overall recovery of drug was 26%.

To show that the binding of R77975 is specific, a competition experiment was done with R78206, a tighter binding compound, and the results showed that the assay is capable of selecting the best binder out of a mixture of compounds. 57 μg of P1/Mahoney poliovirus was incubated in a PBS 5% DMSO solution containing $4 \times 10^{-9}$ moles of $^3$H-R77975 and R78206 respectively, corresponding to a drug to pocket ratio of 10:1 for each compound. The concentration of drug used in the incubation was 8 μM. Under these conditions only R78206 is expected to be bound to virus since its minimum inhibitory concentration (MIC) is 8 nM, compared to 3 μM for R77975. After an incubation time of 2 hours at room temperature, the mixture was run through the column. By counting the amount of radioactivity in the void volume, it was possible to determine whether any of the R77975 bound to the virus. As expected, there was no radioactivity associated with virus in the void volume.

2) Assay Detects Binding of Drug with nM MIC

R78206 (Janssen Pharmaceuticals), a more potent analog of R77975, was incubated with viral binding sites, i.e., P1/M. Previous work had shown that this compound bound to the virus inside the hydrophobic pocket of VP1 and prevented viral replication in vitro. In this incubation, the moles of R78206 equaled the moles of pocket sites. The concentration of R78206 in the incubation was 8 μM. R78206 has a molecular weight of 383 and gave an [M+H]+ peak of 384 in the MALDI-TOF mass spectrum from this experiment. As an additional control, this experiment was repeated with no virus present to ensure that the signal was not simply due to some small amount of residual unbound drug, and as expected, no peak was observed at 384.

3) Assay Detects Binders in a Mixture of Compounds with MIC Values Ranging from nM to $\mu$M In this experiment, three Janssen analogs, R77975, R78206, and R80633, were incubated with virus. All compounds were present in equimolar amounts and there were exactly enough sites to bind all of each compound. To be more precise, there were $6\times10^{-9}$ moles of binding sites and $2\times10^{-9}$ moles of each compound. In a 500 $\mu$L volume, the drug concentration was 4 $\mu$M. After an overnight incubation at 4° C., the incubation was assayed and the resulting MALDI-TOF mass spectrum contained only three peaks corresponding to the three compounds (FIG. 2).

4) Ability of Assay to Discriminate Between Binders and Non-binders

To ensure that the binding of drug to virus was specific, we constructed a test library containing two drugs with proven anti-viral activity, R78206 and R80633, alongside a cocktail of structurally related compounds with no expected ability to bind virus (as shown in earlier crystallographic experiments). In this incubation, each compound was present in an equimolar amount and there were exactly enough pockets to bind all of each compound. The MALDI-TOF spectrum from this experiment indicated the expected peaks for R78206 and R80633. Of the other five compounds, a peak was detected for one, indicating that it may in fact be a weak binder. All other parent molecular weight ion peaks were absent.

5) Library A+Virus

A library of 75 potential ligands was synthesized using combinatorial chemistry. The design of this library was based upon extensive computer modeling on poliovirus and rhinovirus (Joseph-McCarthy, D. et al., Proteins 29:32–58 (1997)). An incubation was set up such that the concentration of the library was 15-fold greater than the concentration of virus binding sites. Specifically the concentration of library A was $3.24\times10^{-4}$ M in the incubation, while the concentration of virus sites was $2.16\times10^{-5}$ M. Given the amount of virus relative to compounds used in this assay, there should be enough sites to bind up to approximately 5 compounds.

After subjecting this incubation to the binding assay, the concentrated sample was analyzed by both electrospray and MALDI-TOF MS. In the MALDI-TOF spectrum, there were in fact 5 peaks and 1 weak peak that could correspond to compounds in the library. The electrospray spectrum showed five relatively strong peaks which corresponded to compounds in the library as well, three of which were also present in the MALDI-TOF spectrum. There were 4 additional weak peaks in the electrospray mass spectrum that could correspond to compounds in the library, one of which also appeared as a weak signal in the MALDI-TOF spectrum. In total, 7 reasonable peaks from both sets of spectra that could correspond to library compounds were identified. These individual compounds will now be synthesized and confirmed for binding by using more stringent assays ( e.g., immunoprecipitation, cell-based, fluorescence, and crystallographic).

In order to confirm the results from the Library A screen, a six compound library that is a subset of Library A was combinatorially synthesized. This six compound library contains two of the potential Library A binders from the previous screen. One milligram of virus was incubated with a PBS/5% DMSO solution containing $5.7\times10^{-4}$ M of the six compound library (roughly 10 $\mu$M per compound), corresponding to a library to pocket ratio of 4:1. After an overnight incubation at 4° C., the incubation was run through the size exclusion column and fractions 7 to 13 were extracted, concentrated, and analyzed by mass spectroscopy. The library is expected to contain compounds with molecular weights 280, 292, 304, 367, 379, and 454. The spectrum identified four potential binders.

6) A Hybrid Split-Pool Synthesis Approach

An alternative approach to screening compounds in combinatorial libraries involves the generation of multiple libraries, each containing approximately 5 to 10 compounds. This approach avoids difficulties in controlling the relative representation of individual members of the larger (approximately 100 compound) libraries and the relatively low signal to noise ratio in mass spectroscopic analyses when larger libraries are used.

Figure 3:
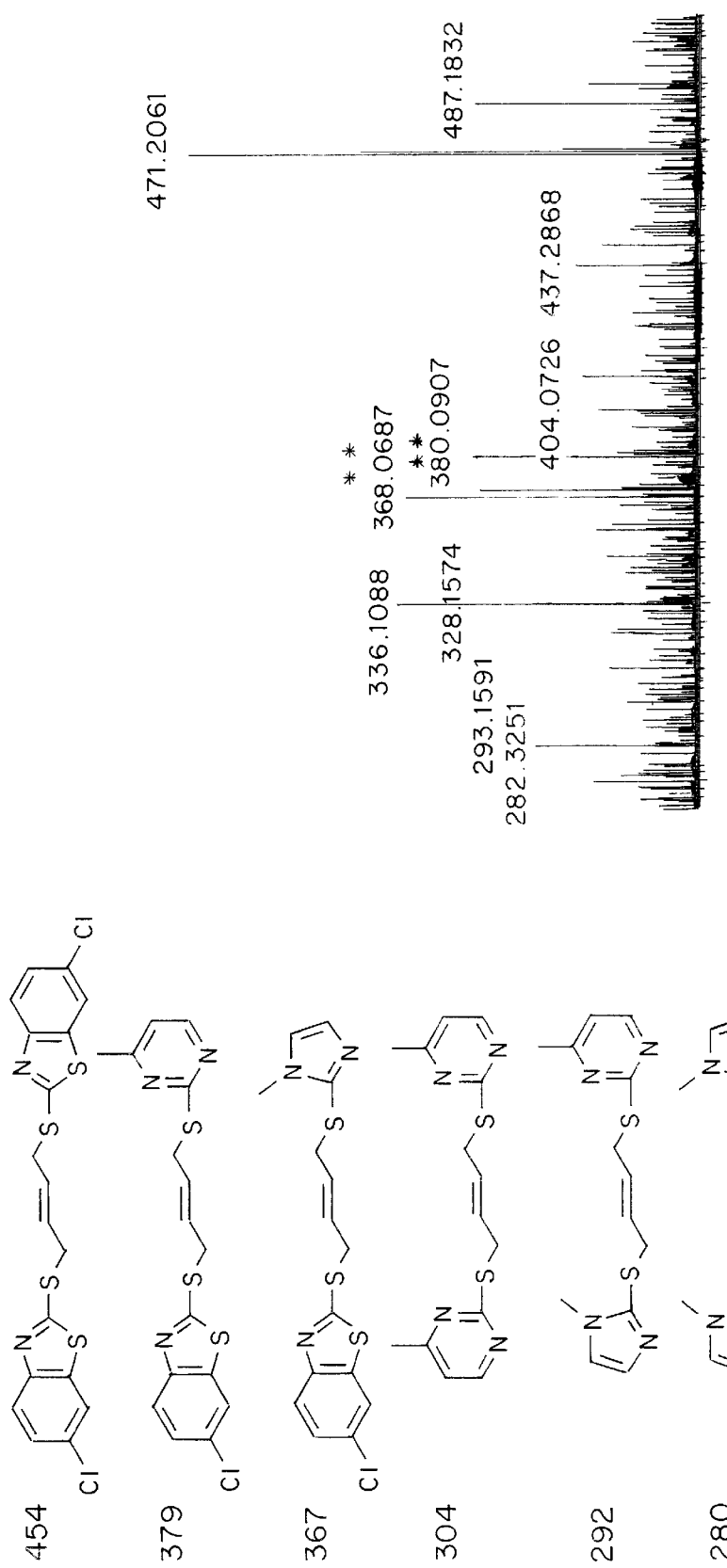
FIG. 3 shows the members of Library 6.1 and mass spectroscopy of a virus binding assay of that library.
Figure 4:
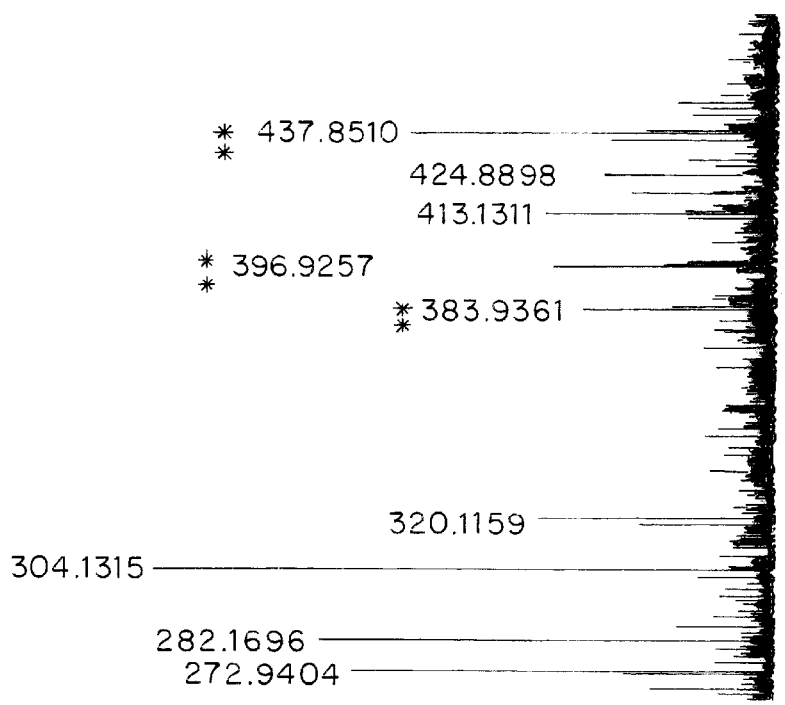
FIG. 4 shows the members of Library 6.2 and mass spectroscopy of a virus binding assay of that library.
Figure 4:
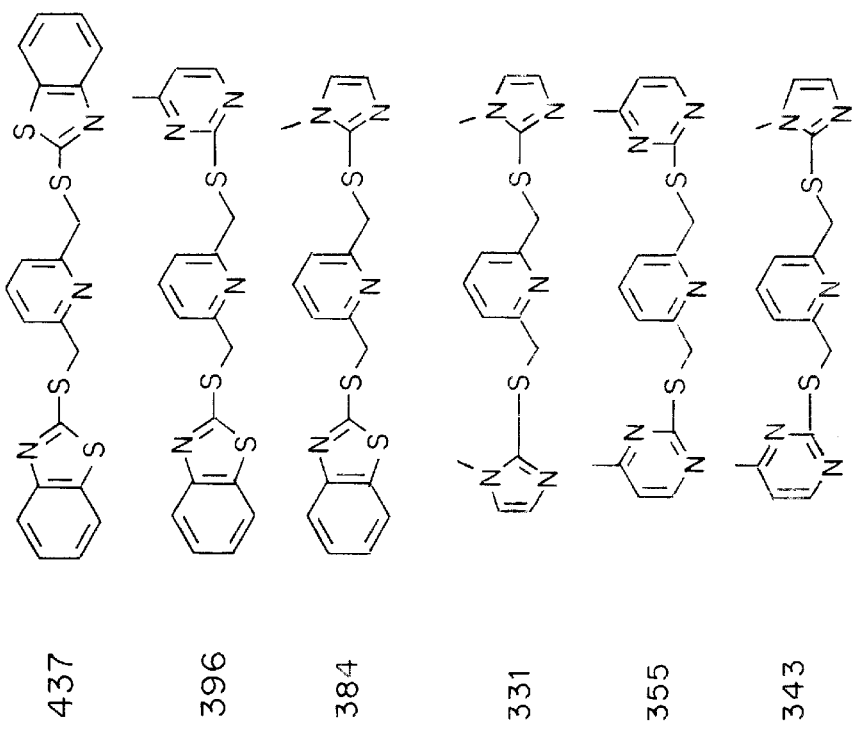

To test this approach, two small libraries containing six compounds each, termed Libraries 6.1 and 6.2, respectively, were synthesized (FIGS. 3 and 4) and tested for viral binding. The mass spectroscopic assay provided convincing evidence that two compounds from Library 6.1 and three compounds from Library 6.2 bind to the virus (FIGS. 3 and 4). In addition to increased control over the synthesis and improved signal to noise in the assay, the hybrid split-pool approach has the advantage that each of the sublibraries may be designed to ask a specific question about modification of a portion of the candidate ligand. Indeed, Library 6.1 was originally designed to explore the consistent hits from library A, and Library 6.2 was designed to address the role of large aromatic versus small aliphatic linkers in the central region of the molecule.

Relatively large numbers of such small libraries may be synthesized simultaneously, and the results analyzed by the sparse matrix and limited factorial approaches that have become popular in other complex multidimensional searches, including crystallization (Schumacher, T. N. et al., 1996, Science 271: 1854; Shuker, S. B., et al., 1996, Science 274: 1531; Smith, T. J. et al., Science 233: 1286). The results of the first round could then be used to design the next generation of multiple small libraries that either probe promising areas of ligand space on progressively finer matrices, or address problems (e.g. solubility or toxicity) which have been identified in the previous round.

7) A Functional Assay for Screening Libraries

Although the mass spectrometry assay has proved very useful in identifying ligands that bind virus it does not address the question of whether the observed binding is functional. Therefore, a secondary functional assay was developed. A test for the ability of compounds to inhibit viral infectivity, for example a tissue culture assay such as that described by Grant, R. A. et al., 1994, Curr. Biol. 4: 784 (the method of which is herein incorporated by reference) may be used. However, this assay is delicate and somewhat cumbersome and requires rigorous purification of ligands to avoid toxicity of reactants and by-products. An indirect assay that measures the ability of ligands to interfere with the conformational conversion of the virus from its native, 160S state to the 135S infective form has therefore been developed. The assay is based on the observation that virus can be efficiently converted to the 135S form in the absence of receptor by heating in hypotonic buffers in the presence of low levels of $Ca^{+2}$.

Figure 5:
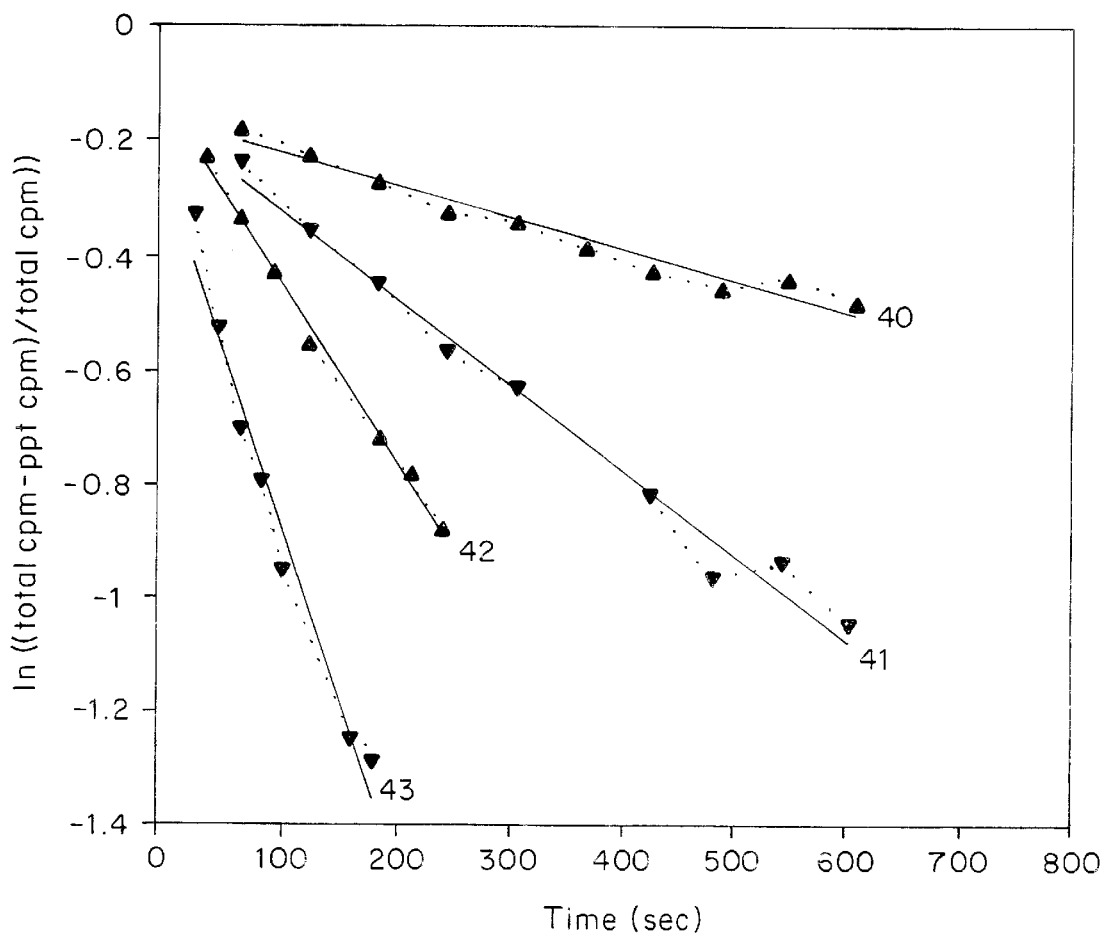
FIG. 5 shows a plot of the results of an immunoprecipitation-based viral inhibition assay.

The assay involves immunoprecipitation using antibodies directed against a peptide corresponding to residues 21–40 of VP1. This region is exposed during the native-135S transition, such that the antibody can only recognize the 135S, and not the native form of the virus. Preliminary studies showed that the rate of conversion of native (unliganded) virus varied steeply as a function of temperature (FIG. 5) and that the rate is significantly reduced by binding drugs with known antiviral activity. The assay measures the rate of conversion at 43° C. where the rates for native virus and virus-R78206 complexes are both within the practical limits of the assay. Briefly, radiolabeled virus is incubated with a compound or library of compounds and then diluted into prewarmed buffer at 43° C. At several time points, aliquots are removed and quenched in chilled buffer. Antisera specific for the amino terminus of VP1 are then added and incubated for 30 min at room temperature. Complexes of antibody with altered virus are then precipitated with protein A beads. The precipitate and supernatant are counted and the first order rate of conversion is calculated from the slope of the best fit line in a plot of log ((total counts–counts precipitated)/total counts) vs time.

Figure 6:
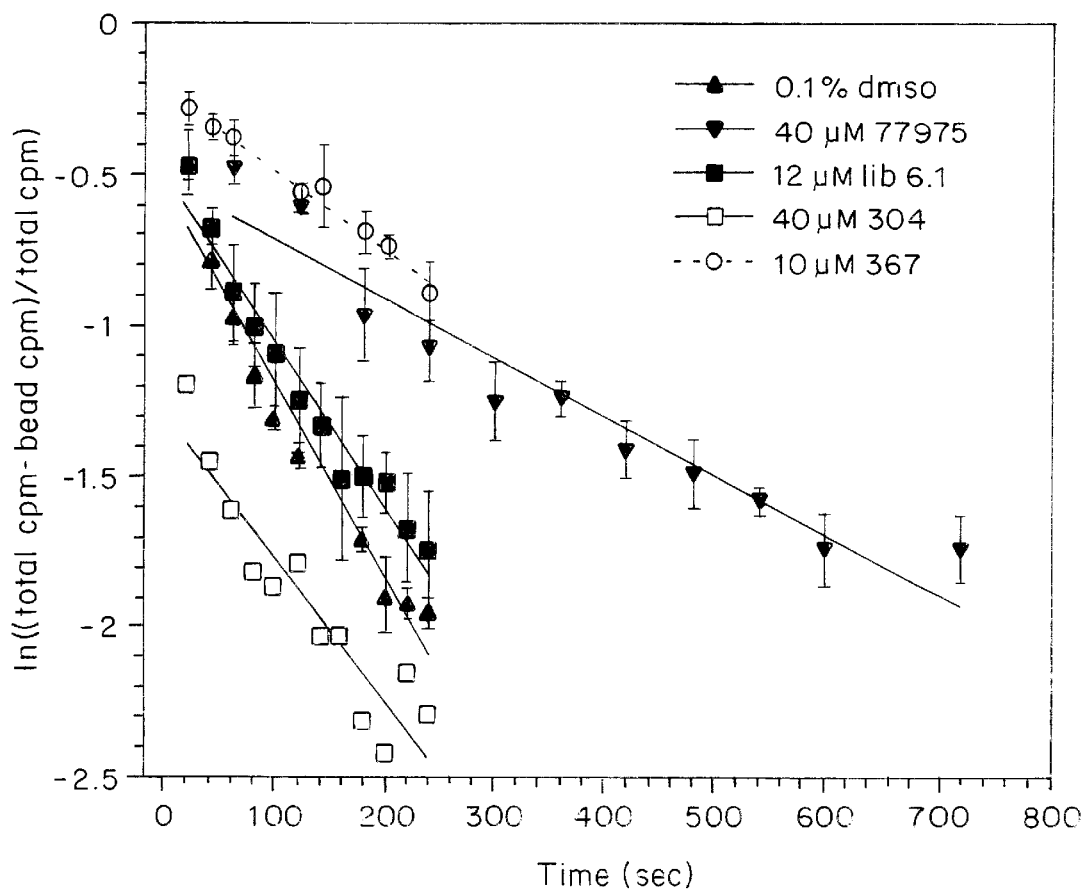
FIG. 6 shows data from a set of viral inhibition assays.

The immunoprecipitation assay has been used to characterize the effect of the 6.1 and 6.2 libraries, as well as three individual compounds from the 6.1 library, on the rate of the native-135S conversion. Two of the purified compounds (304 and 367) had been identified as virus binders in the mass spectroscopy assay. The third (454) was not represented in the library. When synthesized separately the 454 compound was shown to be highly insoluble in most solvents tested, which probably accounts for its failure to be produced in the original library. It was soluble in 0.1% methyl-pyrillodone. Both of the libraries (data for 6.1 are shown) and the 304 and 367 compounds produced modest but highly significant reductions in the rate of conversion at 43° C. (see Table 1 and FIG. 6 ). The individual compounds 304 and 367 showed more dramatic rate reductions. The rate decrease for the 454 compound is even more impressive (even when the protective effect of the solvent is discounted), and the concentration quoted (50 uM) is likely to be a gross over estimate of the true concentration of the drug because of its very limited solubility.

8) Crystallographic Assay Confirms Binding in Normal Drug Binding Pocket

Crystallographic studies of complexes of the candidate ligands with P1/M virus have been performed. To date nearly complete data sets have been collected from crystals soaked in candidate ligands 367 and 304. Data from the 367 complex have been processed, and the structure solved by molecular replacement. The resulting electron density maps clearly show that the ligand is present in the pocket at high occupancy. This confirms that the screening method of the invention is effective in the identification of compounds which bind in the ligand binding pocket of the virus.

9) Stabilization of Virus is Entropically Determined

Figure 7:
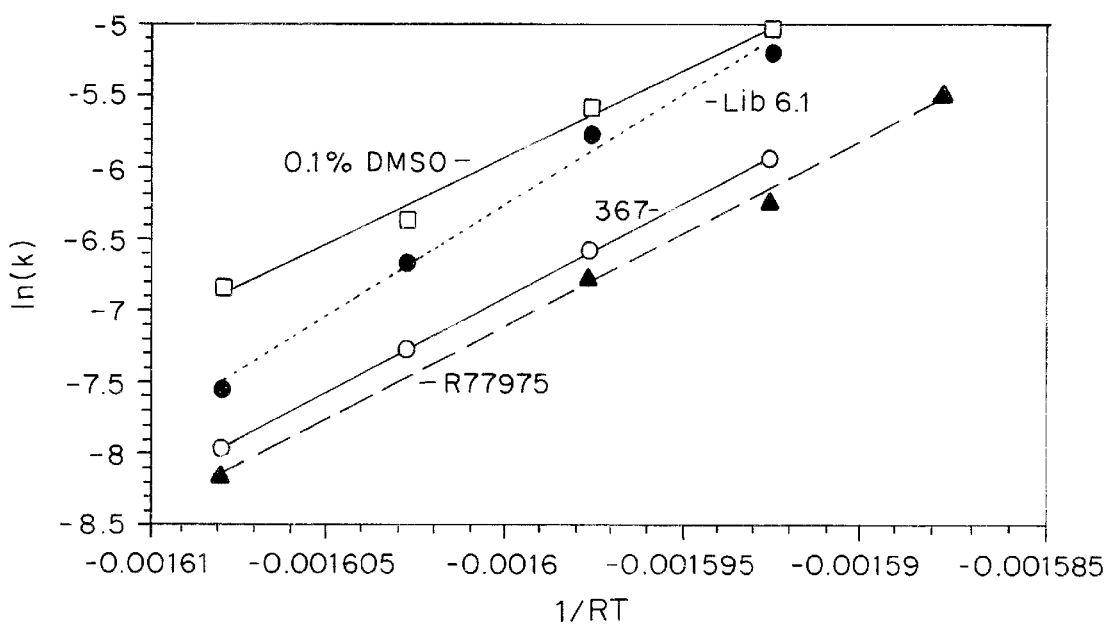
FIG. 7 shows an Arrhenius plot for virus and drug complexes.

The very steep dependence of the first order rate of the native to 135S transition on temperature implies that the activation enthalpy is very high. Indeed, Arrhenius analysis of the dependence of 1 n(k) vs 1/RT yields an activation enthalpy of approximately 120 kcal/mole (FIG. 7). Previous models for the mechanism of drug action had assumed that the drugs would work by increasing the "stiffness" of the VP1, thereby increasing the activation enthalpy and decreasing the rate of conversion. However, when similar data are plotted for a variety of virus-complexes, the data fall on parallel lines (FIG. 6), indicating that the enthalpy of activation is identical (or nearly identical) to that of free virus. This means that the predominant effect of drug binding on rate of conversion is Entropically derived. Helps and Post, 1995, J. mol. Biol. 254: 544, reached a similar conclusion from molecular dynamics simulations of free rhinovirus and rhinovirus drug complexes.

10) Infectivity Inhibition Assay

The definitive in vitro assay for antiviral activity is an assay that measures a compound's ability to inhibit a virus' ability to lyse cells in culture. A number of variations of this assay have been developed and published. A version of the assay used by Jensen was adapted for use in these screening approaches. Briefly, serial five-fold dilutions of compounds are added directly to a 96 well microliter plate. Approximately 100 TKT of virus is then added to each well and incubated at 37° C. After two hours 100 HeLa cells are added to each well and the plate is incubated for 3 days at 37° C., then stained with crystal violet. The minimum inhibitory concentration is defined as the concentration of drug required to reduce the cytopathic effect by 50%.

As these preliminary experiments show, the technique described above is effective in identifying new potential anti-picornaviral compounds. The merging of computational drug design methods and combinatorial chemistry allows for the design and rapid synthesis of structure-based libraries of potential ligands. The assay of the invention is a sensitive method, capable of rapidly screening such libraries within hours. It is also possible to extend this technique to screen for ligand binding in other virus systems. This method may be generally used to screen for binding to any nonenveloped virus (including picornaviruses, calciviruses, paroviruses, papoviruses (e.g., papillomaviruses), retroviruses and adenoviruses) whose intact virions may be isolated by techniques obvious to those skilled in the art (Luria, S. E. et al., supra; Fields, B. N. et al., supra), or for any enveloped virus (including hepatitis B virus, alpha and flaviviruses, herpes viruses, and retroviruses (including HIV)) which contain a stable nucleocapsid particle which can be isolated by those skillful in the art (Luria, S. E. et al., supra; Fields, B. N. et al., supra). Once these potential leads have been identified by this preliminary screen, they can be individually synthesized and subjected to a battery of in vitro and in vivo tests to confirm their potency.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

TABLE 1

Rate Constants at 43° C.

| Compound | k ($10^{-5}$ s$^{-1}$) |
| --- | --- |
| 0.1% | 640 ± 23 |
| 40 μM 77975 | 195 ± 3 |
| 12 μM 6 cpd | 550 ± 49 |
| 40 μM 304 | 470 |
| 10 μM 367 | 260 ± 27 |
| 1% methyl pyrillodone | 269.9 |
| 50 μM 454 | 62.8 |

What is claimed is:

1. A method for screening compounds to determine anti-viral activity, comprising the steps of:
   incubating in vitro a mixture of two or more compounds with a viral site;
   allowing at least one of the two or more compounds to bind to the viral site;
   separating the at least one of the two or more viral site-bound compounds from an unbound compound;
   denaturing the viral site to release the compound from the viral site;
   detecting the at least one of the two or more released compounds; and
   testing the at least one of the two or more released compounds for anti-viral activity.

2. The method of claim 1 wherein the viral site is contained within a virus.

3. The method of claim 2 wherein the virus is a picornavirus.

4. The method of claim 3, wherein the picornavirus is selected from the group consisting of poliovirus, rhinovirus, Coxsackie B virus, Coxsackie A virus, echovirus, and human enterovirus.

5. The method of claim 1 wherein the viral site is contained within a viral capsid.

6. The method of claim 5 wherein the viral site is a conserved hydrophobic pocket at the core of VP1.

7. The method of claim 1 wherein the released compound is detected via mass spectroscopy.

8. The method of claim 1 wherein the number of compounds is less than or equal to the number of viral sites.

9. The method of claim 1 wherein the number of compounds is in excess of the number of viral sites.

10. The method of claim 1, wherein the testing for anti-viral activity is performed using a tissue culture assay or an immunoprecipitation assay.

11. The method of claim 1, wherein the testing for anti-viral activity is performed by measuring the ability of the at least one of the two or more released compounds to inhibit a virus's ability to lyse cells in culture.

12. A method for screening compounds to determine anti-viral activity, comprising the steps of:
   incubating in vitro a mixture of two or more compounds with a viral site;
   allowing at least one of the two or more compounds to bind to the viral site;
   separating the at least one of the two or more viral site-bound compounds from an unbound compound;
   extracting the at least one of the two or more bound compounds into an organic phase,
   whereby the viral site is denatured and bound compound is released from the viral site;
   detecting the at least one of the two or more released compounds; and
   testing the at least one of the two or more released compounds for anti-viral activity.

13. The method of claim 12, wherein the testing for anti-viral activity is performed using a tissue culture assay or an immunoprecipitation assay.

14. The method of claim 12, wherein the testing for anti-viral activity is performed by measuring the ability of the at least one of the two or more released compounds to inhibit a virus's ability to lyse cells in culture.

15. The method of claim 12, wherein the viral site is contained within a virus.

16. The method of claim 15, wherein the virus is a picornavirus.

17. The method of claim 16, wherein the picornavirus is selected from the group consisting of poliovirus, rhinovirus, Coxsackie B virus, Coxsackie A virus, echovirus, and human enterovirus.

18. The method of claim 12, wherein the viral site is contained within a viral capsid.

19. The method of claim 18, wherein the viral site is a conserved hydrophobic pocket at the core of VP1.

20. The method of claim 12, wherein the released compound is detected via mass spectroscopy.

21. The method of claim 12, wherein the number of compounds is less than or equal to the number of viral sites.

22. The method of claim 12, wherein the number of compounds is in excess of the number of viral sites.

\* \* \* \* \*

UNITED STATES PATENT AND TRADEMARK OFFICE
CERTIFICATE OF CORRECTION

| | |
|---|---|
| PATENT NO. | : 6,558,899 B1 |
| APPLICATION NO. | : 09/210118 |
| DATED | : May 6, 2003 |
| INVENTOR(S) | : Tsang et al. |

It is certified that error appears in the above-identified patent and that said Letters Patent is hereby corrected as shown below:

In the Specification

Please delete the paragraph beginning at Column 1, Line number 6 and replace it with the following paragraph:
GOVERNMENT SUPPORT
This invention was made with government support under AI032480 and AI020566 awarded by the National Institutes of Health. The government has certain rights in the invention.

Signed and Sealed this
Thirty-first Day of December, 2024

Derrick Brent
*Acting Director of the United States Patent and Trademark Office*